United States Patent [19]

Gustavsson et al.

[11] 4,397,091

[45] Aug. 9, 1983

[54] DISPENSING CONTAINER FOR VENUS CATHETERS

[76] Inventors: Bengt Gustavsson, Bergsbogatan 29, Västra Frölunda, Sweden, 421 79; Johan Curelaru, Dr. Lindsgata 3, Göteborg, Sweden, 413 25; Lars-Erik Linder, Varbergsvägen 319, Billdal, Sweden, 427 00

[21] Appl. No.: 313,990

[22] Filed: Oct. 22, 1981

[30] Foreign Application Priority Data

Oct. 22, 1980 [SE] Sweden ................................ 8007400

[51] Int. Cl.³ .......................... G01B 3/00; A61M 5/00
[52] U.S. Cl. ....................................... 33/127; 33/138; 128/657
[58] Field of Search ................ 33/127, 138, 139, 140, 33/137 R; 128/656, 657, 658, 772; 242/84.8, 96

[56] References Cited

U.S. PATENT DOCUMENTS

| 261,626 | 7/1882 | Perry et al. | 33/140 |
| 537,082 | 4/1895 | Stuart | 33/139 |
| 692,756 | 2/1902 | Baldwin | 33/139 |
| 3,888,011 | 6/1975 | Hunt, Jr. | 33/139 |

FOREIGN PATENT DOCUMENTS 700 of 1886 United Kingdom ................. 33/140

Primary Examiner—Willis Little
Attorney, Agent, or Firm—Holman & Stern

[57] ABSTRACT

A container for the sterile storage and dispensing of a catheter intended for insertion into a blood vessel is provided with an outlet opening for dispensing the catheter therethrough and has rotatable means for feeding the catheter out through said outlet and indicating means operatively connected to the feeding means for indicating the length of catheter dispensed through the outlet.

4 Claims, 11 Drawing Figures

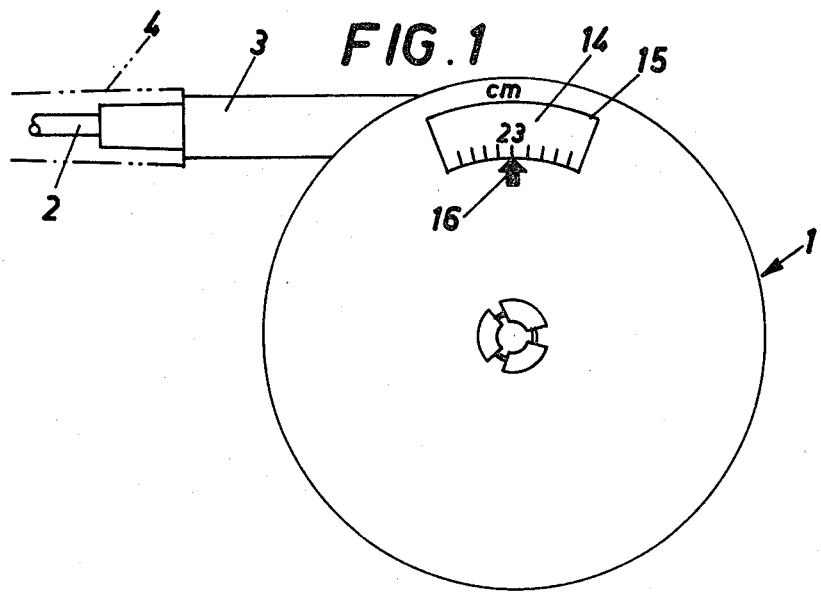
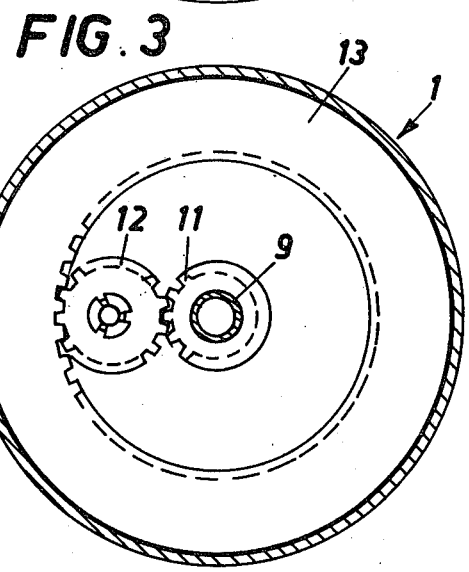
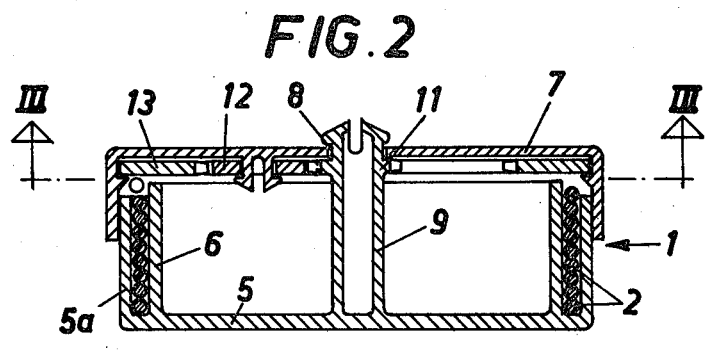

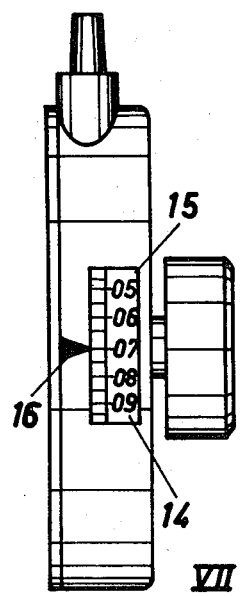
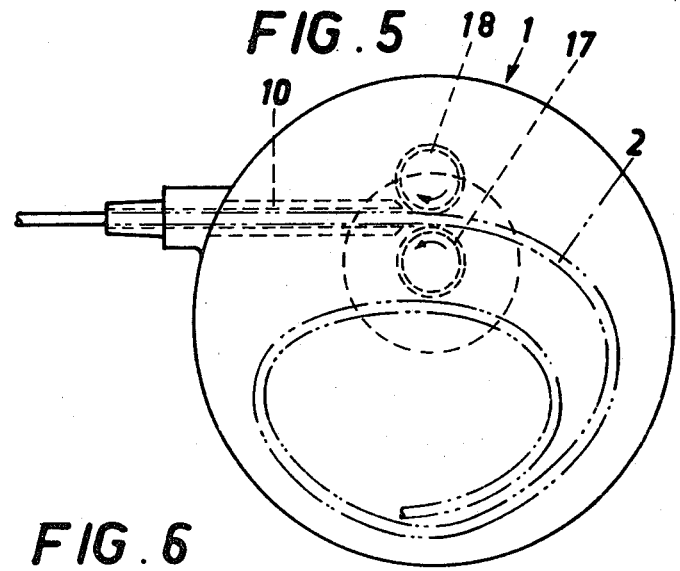
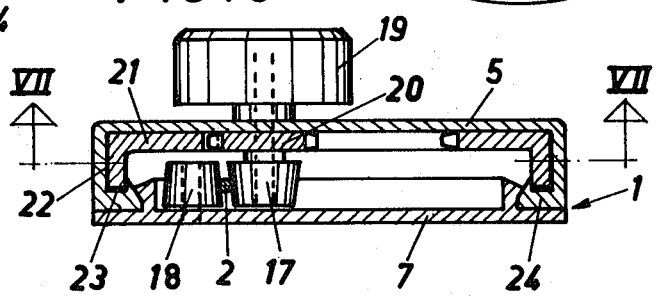
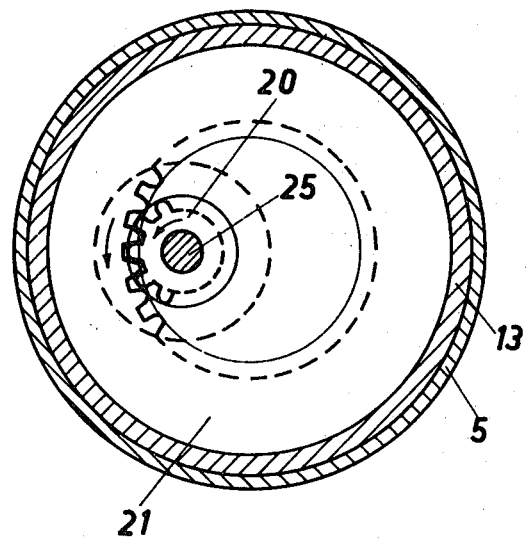

DISPENSING CONTAINER FOR VENUS CATHETERS

BACKGROUND OF THE INVENTION

1. Field of the Invention

The present invention relates to containers for the sterilized storage and dispensing of a catheter intended for insertion into a blood vessel.

2. Description of the Prior Art

The use of central venous catheters is a daily routine during major surgical operations and in post-operational wards. The supply of fluid and nutrition and the taking of blood samples is facilitated by the use of these catheters both for the staff and for the patient. It is of great importance that the catheter is maintained in a sterile condition during the advancement into the vein which is made through a cannula which has been inserted into the vein. Since the catheters have a length of several hundreds of millimeters it is difficult to ensure the sterile condition without the use of special packagings from which the catheters may be fed directly through the cannula by means of a manually operable feeding means. In this manner the catheter will remain unexposed, thereby avoiding the risk of contamination.

Such a combined packaging and feeding device as shown in the U.S. Pat. No. 3,561,445. The catheter is coiled around an arcuate flange in a container, and by rotating the container relative to the lid the catheter will be fed through an outlet opening in the lid and further through a cannula connected to said outlet opening.

With this known device it is not possible to determine the length of the dispensed portion of the catheter except by the use of a graduation applied directly to the catheter, allowing the length of catheter advanced into the blood vessel to be determined by checking the length of catheter remaining in the container. However, it is very difficult to apply an easily readable graduation on a catheter, partly due to the small diameter of the catheter and partly due to the fact that any graduation markings may cause irregularities in the surface of the catheter which must be completely smooth in order to keep thrombus formation as low as possible. Furthermore, any markings on the catheter must be resistant to being dissolved by the blood.

BRIEF SUMMARY OF THE INVENTION

However, in connection with the use of central venous catheters it is highly desirable to be able to determine in a simple way the length of catheter that has been advanced into the blood vessel. It would thereby be possible to obtain a correct position of the tip of the catheter and such complications would be avoided that are connected with a too low or too high position of the catheter tip in the central venous system.

Furthermore, relocation of the catheter would be avoided, thereby also avoiding the risk of bacteria contamination. A correct positioning of the catheter may be obtained also in the absence of X-ray equipment and personnel for controlling the position of the catheter in the central venous system, which is of great importance in emergency conditions, mass casualties, during the performance of surgical interventions etc.

Since the correct location of the catheter tip is of utmost importance, surveys have been made on the population for determining the distance between various puncture sites and the locations where the catheter tip is to be placed. For instance, it has been shown that for the basilic vein of the right arm the distance between the puncture site in fossa cubiti and the junction between superior vena cave and the right atrium is 48.78±0.29 centimeters for women and 52.90±0.27 centimeters for men. It is important that the tip of the catheter reaches the correct location, but if the catheter is advanced too far the heart may be damaged. For these reasons, a mechanism for the accurate measurement of the length of the catheter inserted into the central venous system brings about very important advantages and vastly improves the results of such catheterization.

The main object of the present invention is to provide a container for the sterile storing and dispensing of a catheter and containing a device for giving a direct reading of the length of catheter fed out of the container.

BRIEF DESCRIPTION OF THE DRAWINGS

The invention will be more closely described herebelow with reference to some embodiments illustrated in the accompanying drawings, wherein:

FIG. 1 is a side elevation view of a device according to one embodiment of the invention, FIG. 2 is a diametral cross-sectional view through the device according to FIG. 1, FIG. 3 is a cross-sectional view taken on the line III—III in FIG. 2, FIG. 4 is an end elevational view of another embodiment of the invention, FIG. 5 is a side view of the device according to FIG. 4, FIG. 6 is diametral a cross-sectional view through the device of FIG. 5, FIG. 7 is a cross-sectional view taken along the line VII—VII in FIG. 6.

DETAILED DESCRIPTION

Figure 8:
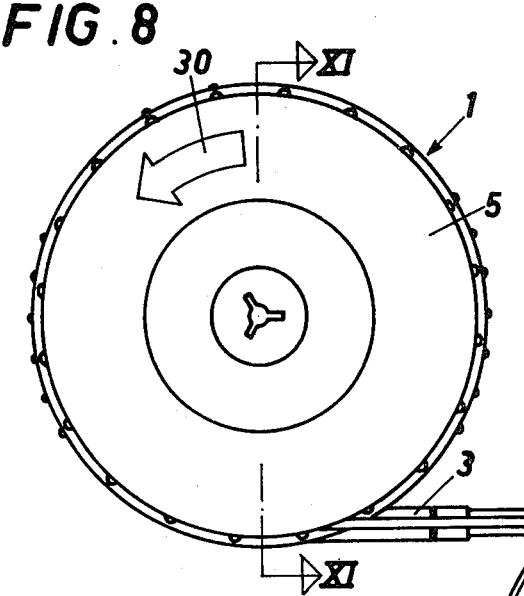
FIG. 8 is a side elevational view of a device according to a further embodiment of the invention.

In the embodiment illustrated in FIGS. 1–3 the device consists of a cylindrical container 1 in which the catheter 2 is coiled up. The container 1 is provided with an outlet 3 to which e.g. a cannula fitting 4 may be connected. The intention is that the catheter 2 may be fed through the outlet 3 and further through the cannula without being exposed.

The container 1 comprises two parts, one of which consists of a drum 5 open towards one end and having a periferal flange 6 at some distance from the side wall of the drum. The catheter 2 is coiled around the flange 6. The other part 7 of the container 1 forms a lid for the first part 5 and has a centrally located opening 8 intended to receive a hub 9 which extends from the bottom of the first portion 5 and which by snap action may be removably fixed in axial direction in the opening 8. The parts 5 and 7 of the container may thereby be rotated relative to each other. The outlet 3 is preferably formed integrally with the lid and consists of a cylindrical passage and a groove 10 (FIG. 5) formed in the lid 7 connected to said passage and guiding the catheter 2 into the outlet and cannula fitting.

The catheter 2 is fed through the outlet 3 by rotating the drum 5 relative to the lid 7. The catheter 2 which usually is elastic and comparatively stiff in order to facilitate the insertion into the blood vessel will be pressed against the side wall of the drum 5 when lying coiled up in the drum. The friction between the catheter and the side wall of the drum will then be sufficient to prevent a relative movement between them.

The hub 9 is provided, at some distance from its free end, with a gear ring 11 which is preferably formed integrally with the hub. The gear ring 11 is in meshing engagement with a gear wheel 12 rotatably guided at the inner side of the lid 7. The gear wheel 12 in turn engages an internally geared ring 13 guided in the side wall of the lid 7. The gear ring 13 is provided with a graduation 14 corresponding to the dispensed length of catheter. The graduation 14 is readable through a window 15 in the lid 7 which is provided with a mark 16 against which the length of catheter fed out is red. If the container is made of transparent material, no window is needed.

In the embodiment illustrated in FIGS. 4–7 the catheter 2 is loosely coiled inside the container 1 and is fed between two slightly conically tapered rubber rollers 17 and 18 or the like to the outlet 3. One roller 17 is rotatable by means of a knob 19 journalled eccentrically on the drum. On the same shaft 25 as the roller 17 there is also provided a gear wheel 20 which acts upon a gear ring 21 guided against the inside of the side wall of the part 5. The gear ring 21 has a periferal flange 22 at right angles to the plane of the ring and forming a guide for the ring. The free edge portion of the flange 22 is guided in a groove 23 in an inwardly turned circumferential collar 24 of the part 5. The lid 7 is snapped in position engaging said collar. The other roller 18 is rotatably journalled in the lid 7.

By rotating the knob 19 the catheter 2 will be fed between the rollers 17 and 18 and the length of the fed-out portion of the catheter may be read through a window 15 provided in the side wall of the part 5, the graduation 14 being provided on the flange 22 of the gear ring 21. The fed-out length of the catheter may conveniently be read during the feeding out, the container being held in the position illustrated in FIG. 4.

If the roller 18 is journalled in the part 5 instead of in the lid 7, the lid may be eliminated and instead a plastic bag or the like may be attached to the part 5 for containing the catheter 2.

Figure 9:
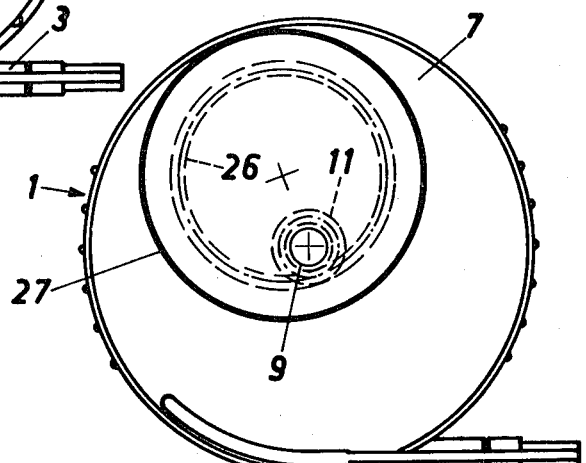
FIG. 9 is a view corresponding to FIG. 8 but with one part of the container removed for showing the inside of the device.
Figure 10:
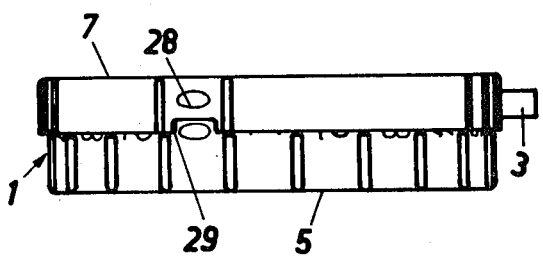
FIG. 10 is an end elevational view of the device according to FIGS. 8 and 9.
Figure 11:
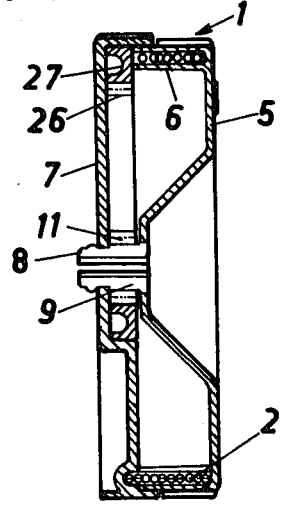
FIG. 11 is a cross-sectional view taken along the line XI—XI in FIG. 8.

In the embodiment shown in FIGS. 8–11 the gear wheel 11 formed integrally with the hub portion 9 of the drum 5 engages the gears 26 of a gear ring 27 which is rotatably seated in a circularly depressed portion of the lid 7. As in the embodiment of FIGS. 1–3 the container is held by the lid 7 and the drum part 5 is rotated relative thereto (in the direction of the arrow 30 in FIG. 8) for feeding the catheter 2 out through the outlet 3. The circular wall of the drum 5 is provided on its outside with a graduated scale indicating length units, and the figures of the scale are visible when opposite a notch 29 in the free edge portion of the periferal flange of the lid 7. The outer ring of the gear ring 27 is also provided with a graduation visible through an opening 28 adjacent the notch 29 in the flange of the lid 7. The graduated scale of the ring 27 covers the total length of the catheter 2 contained in the container, and finer readings can be made on the scale provided on the outside of the drum 5, the latter scale, being divided e.g. into millimeters.

The invention is not limited to the embodiments hereinbefore described and as shown in the accompanying drawings, various modifications thereto being possible within the scope of the appended claims.

We claim:

1. In a container for the sterile storage and sterile dispensing of a catheter intended for insertion into a blood vessel wherein the catheter is stored in the container and the container is a hollow casing comprising an open-ended drum part and a lid part closing the open end of the drum part and rotatably interconnected therewith having an outlet opening for dispensing the catheter therethrough and wherein a rotatable feeding means is provided comprising two concentrically spaced peripheral walls in the drum part forming a peripheral annulus in which the catheter is helically coiled so that rotation of the drum part with respect to the lid part in the feeding direction causes the catheter to advance out through the outlet so that the length of catheter being dispensed is proportional to the angle of rotation of the drum part, the total length of the catheter corresponding to more than one revolution of the drum part, the improvement comprising at least one rotatable indicating means rotatably mounted in said container, indicia showing units of length on said indicating means for indicating the length of catheter dispensed through said outlet, means on said container for viewing at least one of said units at predetermined points of rotation of said indicating means, and a reduction transmission operatively connecting said feeding means to said indicating means comprising a first gear wheel fixedly attached concentrically to said drum part, to rotate therewith and a ring gear integral with said indicating means rotatably mounted on said lid part and operatively connected with said first gear wheel so that said indicating means is driven by said first gear wheel at a lower speed of revolution than said feeding means and said length units show fractional parts of the total feeding means, said indicia being graduated to cover the total length of the catheter.

2. The improvement as claimed in claim 1 and wherein said reduction transmission further comprises a second gear wheel rotatably mounted on said lid in meshing engagement with said first gear wheel and said ring gear.

3. The improvement in a container as claimed in claim 1 wherein said ring gear is rotatably mounted on said lid part in meshing engagement with said first gear wheel, and wherein said indicating means further comprises second indicia showing second units of length on the outer periphery of said drum part, said second units of length comprising a graduated scale of smaller increments of length than the units of length on said ring gear, and means to read both said units of length simultaneously.

4. In a container for the sterile storage and sterile dispensing of a catheter intended for insertion into a blood vessel wherein the catheter is stored in the container and the container is a hollow casing having an outlet opening for dispensing the catheter therethrough and a rotatable feeding means which when rotated causes the catheter to advance out through the outlet so that the length of catheter being dispensed is proportional to the angle of rotation of the rotatable feeding means, the total length of the catheter corresponding to more than one revolution of the rotatable feeding means, the improvement comprising at least one rotatable indicating means rotatably mounted in said container, indicia showing units of length on said indicating means for indicating the length of catheter dispensed through said outlet, means on said container for viewing at least one of said units at predetermined points of rotation of said indicating means and a reduction transmission operatively connecting said feeding means to said indicating means comprising a first gear fixedly attached to said feeding means to rotate therewith and a ring gear rotatably mounted within said casing operatively engaging said first gear and integral with said indicating means so that said indicating means is driven by said first gear at a lower speed of revolution than said feeding means and said length units show fractional parts of the total length of catheter dispensed by one revolution of said feeding means, said indicia being graduated to cover the total length of the catheter, said feeding means comprising two rollers rotatably journalled in the container in spaced relation to each other for gripping and feeding the catheter therebetween towards and through said outlet opening, a shaft on which one of said rollers is fixedly mounted extending through the casing, a knob provided on the outside of the casing mounted on the extending part of said shaft part of for rotating the shaft, and said first gear comprises a gear wheel mounted on said shaft in meshing engagement with said ring gear.

* * * * *